US00PP25669P3

(12) United States Plant Patent
de Bont

(10) Patent No.: US PP25,669 P3
(45) Date of Patent: Jun. 30, 2015

(54) *ECHINACEA* PLANT NAMED 'ORPASS'

(50) Latin Name: ***Echinacea* hybrid**
Varietal Denomination: Orpass

(71) Applicant: Dionysius F. M. de Bont, Gouda (NL)

(72) Inventor: Dionysius F. M. de Bont, Gouda (NL)

( * ) Notice: Subject to any disclaimer, the term of this patent is extended or adjusted under 35 U.S.C. 154(b) by 309 days.

(21) Appl. No.: 13/986,119

(22) Filed: Apr. 3, 2013

(65) Prior Publication Data

US 2014/0090138 P1 Mar. 27, 2014

(51) Int. Cl.
*A01H 5/02* (2006.01)

(52) U.S. Cl.
USPC ..... Plt./428
CPC ..... *A01H 5/025* (2013.01)

(58) Field of Classification Search
USPC ..... Plt./428
See application file for complete search history.

*Primary Examiner* — June Hwu
(74) *Attorney, Agent, or Firm* — Penny J. Aguirre

(57) ABSTRACT

A new cultivar of hybrid *Echinacea*, 'Orpass', characterized by its inflorescences with deep red cones and ray florets that open clear orange and mature to orange and diffused with red, particularly at base, its very strong stems that are held erect, and its vigorous growth habit.

2 Drawing Sheets

Botanical classification: *Echinacea* hybrid.
Variety denomination: 'Orpass'.

BACKGROUND OF THE INVENTION

The present invention relates to a new and distinct cultivar of *Echinacea* of hybrid origin and will be referred to hereafter by its cultivar name, 'Orpass'. 'Orpass' represents a new coneflower, an herbaceous perennial grown for landscape use.

The Inventor selected the new cultivar, 'Orpass', in a seedbed at a nursery in Sint Annaland, The Netherlands in August of 2008. The seedbed had been planted with seeds collected and pooled from unnamed proprietary plants of *Echinacea purpurea* and unnamed proprietary plants of hybrid *Echinacea*. The exact parents are therefore unknown.

Asexual propagation of the new cultivar was first accomplished by in vitro propagation under the direction of the Inventor in Rijswijk, The Netherlands in September of 2010. Asexual propagation by in vitro propagation has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Orpass' as a unique cultivar of *Echinacea*.

1. 'Orpass' exhibits inflorescences with deep red cones and ray florets that are uniquely colored; opening clear orange and maturing to orange and diffused with red, particularly at base.
2. 'Orpass' exhibits a floriferous habit.
3. 'Orpass' exhibits very strong stems that are held erect.
4. 'Orpass' exhibits a vigorous growth habit.

The new cultivar can be most closely compared to the cultivars 'Evan Saul' (U.S. Plant Pat. No. 17,659) and 'Tangerine Dream' (U.S. Plant Pat. No. 21,773). 'Evan Saul' is similar to 'Orpass' in having ray florets that are orange in color, however 'Evan Saul' differs from 'Orpass' in having ray florets that are paler orange in color, in having a less vigorous growth habit, and in being less floriferous. 'Tangerine Dream' is similar to 'Orpass' in having orange ray florets, however 'Tangerine Dream' differs from 'Orpass' in having ray florets that are more drooping in aspect, stems that are less strong, and in having a shorter plant height.

BRIEF DESCRIPTION OF THE DRAWINGS

The plants in the accompanying photographs depict the characteristics of a six month-old plant of 'Orpass' as field grown in Sint Annaland, The Netherlands and placed in a one-gallon container for the photographs.

The photograph in FIG. 1 provides a side view of a plant in bloom.

Figure 1:
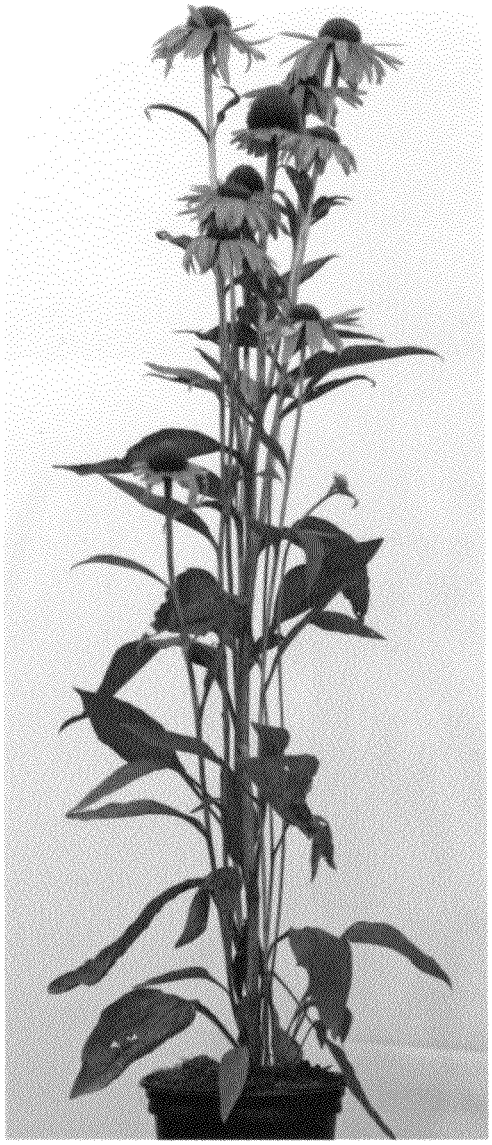
Figure 2:
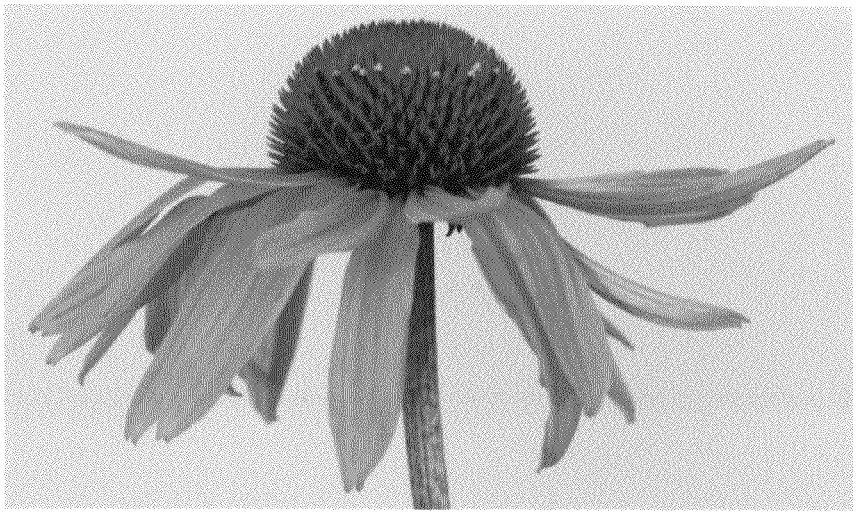

The photograph in FIG. 2 provides a close-up view of an inflorescence of 'Orpass'.

Figure 3:
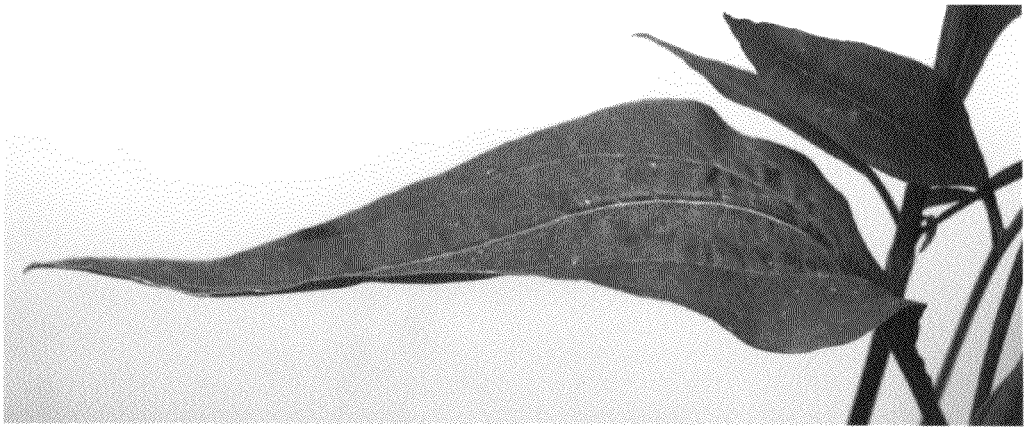

The photograph in FIG. 3 provides a close-up view of a leaf of 'Orpass'.

The colors in the photograph may differ slightly from the color values cited in the detailed botanical description, which accurately describe the colors of the new *Echinacea*.

BOTANICAL DESCRIPTION OF THE PLANT

The following is a detailed description of six month-old plants of 'Orpass' as field grown in Sint Annaland, The Netherlands. Plants were grown under average day temperatures ranging from 15° to 32° C. and average night temperatures of 12° to 20° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—July into September in The Netherlands.

*Plant type*.—Herbaceous perennial.

*Plant habit*.—Clump forming, upright with strong stems.

*Height and spread*.—Reaches 80 to 90 cm in height and an average of 40 cm in spread.

*Cold hardiness*.—At least to U.S.D.A. Zone 3.

*Diseases and pests*.—Not more susceptible to pests or diseases than other *Echinacea* varieties.

*Root description*.—Fibrous.

*Propagation*.—Tissue culture.

*Growth rate*.—Vigorous.

Stem description:

*Shape*.—Rounded.

*Stem color*.—145A, marbled with 146B.

*Stem size*.—Average of 5.5 mm in diameter and an average of 56.8 cm in height.

*Stem surface*.—Slightly rough to the touch due to being very sparsely covered with very short strigose hairs; 1 mm in length and NN155D in color.

*Stem strength*.—Strong.

*Stem aspect*.—Held erect.

*Stem number*.—Average of 7 main stems.

*Branching*.—Un-branched.

Foliage description:

*Leaf shape*.—Ovate to narrowly ovate.

*Leaf division*.—Simple.

*Leaf base*.—Attenuate.

*Leaf apex*.—Long acute.

*Leaf venation*.—Pinnate, upper and lower surface color; 144C.

*Leaf margins*.—Entire to coarsely and shallowly dentate.

*Leaf attachment*.—Petiolate.

*Leaf arrangement*.—Alternate.

*Internode length*.—An average of 7.6 cm.

*Leaf size*.—Average of 14.2 cm in length and 4.6 cm in width.

*Leaf color*.—Young upper surface; 143A, young lower surface; 138A, mature upper surface; 137A, mature lower surface; 137C.

*Leaf surface*.—Upper and lower surface is slightly glossy and moderately covered with very short strigose hairs; average length of 0.5 mm and 155D in color.

*Petioles*.—Upper stem leaves nearly sessile, average length of stem leaves are 4.7 cm in length, v-shaped petiole is about 2.5 mm in length and 2 mm in width, color; upper and lower surfaces 145A, margins 143A, upper and lower surfaces smooth.

Flower description:

*Type*.—Terminal capitulum, heterogamous with ray florets around the head margin and disk florets in the center, forming a radiant head.

*Capitulum number*.—1 to 2 capitulae per stem.

*Lastingness of inflorescence*.—About 10 days.

*Capitulum size*.—Matures to about 6 cm in height and 11.2 cm in diameter, disk size is an average of 3.8 cm in diameter.

*Fragrance*.—Faint, sweet and slightly acidic fragrance.

*Involucral bracts or phyllary*.—About 80 arranged in 3 overlapping rows, up to 7 mm in length and 2 mm in width, dull in appearance, cuneate at base, acute apex, ovate to narrow ovate in shape, entire margins sparsely covered with very short hairs; 0.5 mm in length and 155D in color, upper surface; smooth and 138A, base 138D in color, lower surface; 137A in color.

*Buds*.—Flattened globular in shape, immature ray florets near vertical, 2 cm in diameter and 1.9 cm in length, color; N137A, immature receptacle spines 187A to 187B, immature ray florets 150B to 150C, base N170D.

*Peduncle*.—Strong, straight on top of main. (flowering) stem, average angle of secondary peduncles 20°, terminal peduncle length is 9.3 and 4 mm in diameter, fourth peduncle 12.8 cm in length and 4 mm in diameter, 145A , marbled 146B becoming 147B near the inflorescence, surface is moderately covered with very short strigose hairs, 1 mm in length and NN155D in color.

*Ray florets*.—Rotate, about 27, oblanceolate in shape, about 5.2 cm in length and 1 cm in width, praemorse apex, cuneate base, entire margin, slightly drooping in an average angle of 10° downward, upper surface texture is smooth and velvety and moderately ribbed lengthways (carinate), lower surface texture is smooth and moderately ribbed lengthways (carinate), color: when opening upper surface; 25A, base 20A, when opening lower surface; between 180D and 182D; when fully open upper surface; 25A, base between 32A and 33B, when fully open lower surface; 182C, upper side fading to 26A, base 34B, lower side fading to 182C.

*Disk florets* (*bisexual*).—Numerous, about 360, tubular in shape, fused into tube upper 10% free, acute apex, base fused into tube, about 0.9 cm in length and 2 mm in width, entire margin, upper and lower surfaces smooth and glossy in appearance, color of upper and lower surfaces when opening; 145A, outer tip 178A, color of upper and lower surfaces with fully open; 178A, mid-section 145A, base 145B to 145C.

*Receptacle*.—Triangular in shape, about 1.1 cm in diameter and 1 cm in height; color is NN155A.

*Receptacle spines*.—Average of 360, acicular in shape, acute apex, attenuate base, smooth and glossy surface, color: apex; 46A, mid-section; 23A, base; 144A.

Reproductive organs:

*Gynoecium*.—Pistil; 1.8 mm in length, style; 6.5 mm in length and 145A in color, ovary; 145C in color, presence; on ray and disk florets.

*Androcoecium*.—Stamens; 4, filament 3 mm in length and 150A in color, anther; linear in shape, 3.5 mm in length and 200B in color, pollen is moderate to high in quantity and 15A in color, presence; on disk florets only.

*Fruit/seed*.—No fruit or seed detected to date.

It is claimed:

1. A new and distinct cultivar of *Echinacea* plant named 'Orpass' substantially as herein illustrated and described.

* * * * *